US010674992B2

(12) United States Patent
Konkle et al.

(10) Patent No.: US 10,674,992 B2
(45) Date of Patent: Jun. 9, 2020

(54) SELECTABLE ROI AND FLEXIBLE DETECTOR FOR X-RAY IMAGING

(71) Applicant: General Electric Company, Schenectady, NY (US)

(72) Inventors: Nicholas Konkle, Waukesha, WI (US); Marc Schaepkens, Troy, NY (US)

(73) Assignee: General Electric Company, Schenectady, NY (US)

(*) Notice: Subject to any disclaimer, the term of this patent is extended or adjusted under 35 U.S.C. 154(b) by 291 days.

(21) Appl. No.: 15/719,980

(22) Filed: Sep. 29, 2017

(65) Prior Publication Data

US 2019/0099150 A1      Apr. 4, 2019

(51) Int. Cl.
| | |
|---|---|
| *A61B 6/00* | (2006.01) |
| *G01N 23/046* | (2018.01) |
| *A61B 6/08* | (2006.01) |
| *A61B 6/10* | (2006.01) |
| *H04N 5/369* | (2011.01) |

(52) U.S. Cl.
CPC ............... *A61B 6/587* (2013.01); *A61B 6/08* (2013.01); *A61B 6/4208* (2013.01); *A61B 6/4266* (2013.01); *A61B 6/4275* (2013.01); *A61B 6/4429* (2013.01); *A61B 6/4441* (2013.01); *A61B 6/469* (2013.01); *A61B 6/54* (2013.01); *A61B 6/545* (2013.01); *A61B 6/588* (2013.01); *A61B 6/589* (2013.01); *G01N 23/046* (2013.01); *H04N 5/3698* (2013.01); *A61B 6/102* (2013.01); *A61B 6/547* (2013.01); *G01N 2223/3305* (2013.01)

(58) Field of Classification Search
CPC ..... A61B 6/469; A61B 6/4435; H04N 5/3698
See application file for complete search history.

(56) References Cited

U.S. PATENT DOCUMENTS

| | | | |
|---|---|---|---|
| 2010/0106014 A1* | 4/2010 | Broennimann | ....... A61B 5/1114 600/431 |
| 2017/0227658 A1* | 8/2017 | Steadman Booker | .. G01T 1/243 |
| 2018/0256128 A1* | 9/2018 | Cho | ....................... A61B 6/584 |

* cited by examiner

*Primary Examiner* — Yara B Green
(74) *Attorney, Agent, or Firm* — Boyle Fredrickson, S.C.

(57) ABSTRACT

An imaging system and detector for obtaining x-ray images of a region of interest (ROI) within an object is provided that does not require movement of the detector and/or object/patient for alignment with the x-ray source. The detector is formed with an array of detector elements disposed on a substrate that has an area larger than the area of the objects/patients to be imaged. In use, the object/patient is positioned between the x-ray source and the detector and the x-ray source is targeted at the ROI. The control mechanism determines the area of the detector aligned with the x-ray source and ROI and operates the selected detector elements in the area struck by the x-rays from the source passing through the ROI of the object/patient. The control mechanism receives image data from the area of the detector formed by the detector elements in order to form images of the ROI.

18 Claims, 4 Drawing Sheets

SELECTABLE ROI AND FLEXIBLE DETECTOR FOR X-RAY IMAGING

BACKGROUND OF INVENTION

In order to obtain X-ray images of interior structures of a body, such as a piece of luggage or the body of a patient, various types of imaging systems are employed. In one prior art imaging system illustrated in FIG. 1, an exemplary radiologic imaging system 200 may include a C-arm radiography system 102 configured to acquire projection data from one or more view angles around a subject, such as a patient 104 positioned on an examination table 105 for further analysis and/or display. To that end, the C-arm radiography system 102 may include a gantry 106 having a mobile support such as a movable C-arm 107 including at least one radiation source 108 such as an x-ray tube and a detector 110 positioned at opposite ends of the C-arm 107. In exemplary embodiments, the radiography system 102 can be an x-ray system, a positron emission tomography (PET) system, a computerized tomosynthesis (CT) system, an angiographic or fluoroscopic system, and the like or combination thereof, operable to generate static images acquired by static imaging detectors (e.g., CT systems, MRI systems, etc.) prior to a medical procedure, or real-time images acquired with real-time imaging detectors (e.g., angioplastic systems, laparoscopic systems, endoscopic systems, etc.) during the medical procedure, or combinations thereof. Thus, the types of acquired images can be diagnostic or interventional.

The radiation source 108 includes an emission device configured to emit the x-ray beams 112 towards the detector 110 that includes a plurality of detector elements that may be similar or different in size and/or energy sensitivity for imaging a region of interest (ROI) of the patient 104 at a desired resolution.

The C-arm 107 may be configured to move along a desired scanning path for orienting the x-ray source 108 and the detector 110 at different positions and angles around the patient 104 for acquiring information for 3D imaging of dynamic processes. To control this motion, the C-arm system 102 includes control circuitry 114 configured to control the movement of the C-arm 107 and/or the table 105 along the different axes based on user inputs and/or protocol-based instructions. Control circuitry 114 for the system 200 may include a control mechanism 204 and associated computing device 214 configured to control position, orientation and/or rotation of the table 105, the gantry 106, the C-arm 107 and/or the components mounted thereon in certain specific acquisition trajectories.

The detector 110 may be positioned on the C-arm 107 opposite the x-ray source 108 or can be disposed on or within the table 105 below the area or region of interest of the patient 104 to be imaged. The detector 110 includes a plurality of detector elements 202, for example, arranged as a 2D detector array, for sensing the projected x-ray beams 112 that pass through the patient 104. The detector elements 202 produce an electrical signal representative of the intensity of the impinging x-ray beams 112, which in turn, can be used by the computing device 214 to estimate the attenuation of the x-ray beams 112 as they pass through the patient 104 to provide an image on a display 218, as is known. In another embodiment, the detector elements 202 determine a count of incident photons in the x-ray beams 112 and/or determine corresponding energy. Particularly, in one embodiment, the detector elements 202 may acquire electrical signals corresponding to the generated x-ray beams 112 at a variety of angular positions around the patient 104 for collecting a plurality of radiographic projection views for construction of X-ray images, such as to form fluoro image(s).

In prior art imaging systems 200, the detector 110 is stationary, either relative to the x-ray source 108, as in the illustrated system 200 of FIG. 1, or to a support for the patient 104, i.e., the table 105. By making the detector 110 stationary, it is possible to locate the patient 104, and in particular the region of interest (ROI) to be imaged, in position relative to the detector 110 and then to move the x-ray source 108 in the proper orientation relative to the detector 110 to obtain an image of the ROI.

In these prior imaging systems 200, it is often difficult to properly orient the x-ray source 108 relative to the object or patient 104 to be imaged, particularly when the ROI is covers a relatively large are of the object or patient. This results from the small size of the detectors 110 that are currently utilized, e.g., detectors 110 that are 10"×12" or 40"×41". Further, even when the size of the detector 110 is sufficient to encompass the entire ROI, in order to obtain sufficient images of the ROI for review, it is often necessary to move the object/patient 104 and/or the x-ray source 108 relative to the detector 110, and often to reposition the detector 110 as well, in order to position the x-ray source 108 at the desired angles relative to the ROI to obtain the proper images. The sequential nature of this process to obtain these images results in a very slow and laborious process for obtaining the images. Further, in certain situations, the object/patient 104 cannot be moved, such as where the patient 104 is in critical condition and/or has injuries that prevent the patient 104 from being able to move, which renders the imaging system 202 unable to obtain the desired images of the object/patient 104.

Accordingly, it is desirable to provide an imaging system and associated detector with the capability to accommodate multiple positions of the x-ray source for obtaining images of an ROI without associated movement or positioning of the detector and/or the object/patient to be imaged.

BRIEF DESCRIPTION OF THE INVENTION

There is a need or desire for an imaging system and associated detector capable of obtaining x-ray images of a region of interest (ROI) within an object or patient that does not require movement of the detector and/or object/patient for alignment with the x-ray source. The detector is formed with an array of detector elements capable of detecting the impingement of x-rays to create the x-ray image. The detector elements are disposed on a substrate that has an area larger than the area of the objects/patients to be imaged. In use, the object/patient is positioned between the x-ray source and the detector and the x-ray source is targeted at the ROI to be imaged. Due to the larger size of the detector, it is not necessary to move the detector or the object/patient relative to one another or to the x-ray source. A control mechanism determines the area of the detector aligned with the x-ray source and ROI and operates the selected detector elements in the area struck by the x-rays from the source passing through the ROI of the object/patient. The x-rays generated by the x-ray source pass through the ROI of the object/patient and strike the detector elements. The control mechanism/computing system operably connected to the detector receives image data from the area of the detector formed by the detector elements struck with the x-rays in order to form images of the ROI.

According to another exemplary aspect of the invention, the computing system can also be operated prior to the x-ray source being operated to selectively configure a specific area or areas of the detector to provide the image data to the computing device, optionally in response to a signal identifying the position of the x-ray source relative to the detector. In this manner the detector can be operated to obtain image data regarding one or more ROIs in one or more object(s)/patient(s) positioned between the detector and one or more x-ray sources.

According to a further exemplary aspect of the invention, the detector is formed to be flexible in nature, such that the detector can be placed into a configuration to enable the detector to produce multiple images of the ROI from different angles of the x-ray source relative to the ROI and the detector.

According to still another aspect of the invention. An imaging system includes an x-ray source, an x-ray detector including a number of independently operable detector elements and a control mechanism operably connected to the x-ray source and the detector elements for controlling operation of the x-ray source and the detector elements and receiving image data from the detector elements, wherein the control mechanism is configured to determine an area of detector elements in alignment with the x-ray source and an ROI of an object to be imaged and to operate the detector elements disposed within the determined area.

According to still a further aspect of the invention, a method for obtaining image data of a region of interest (ROI) within an object is provided including the steps of providing an imaging system including an x-ray source, an x-ray detector including a number of independently operable detector elements and a control mechanism operably connected to the x-ray source and the detector elements for controlling operation of the x-ray source and the detector elements and receiving image data from the detector elements, positioning the x-ray source relative to the object to direct x-rays through the ROI, determining an area of detector elements in alignment with the x-ray source and the ROI, operating the detector elements disposed within the determined area and operating the x-ray source to obtain x-ray image data of the ROI from the detector elements in the determined area.

According to still a further aspect of the invention, a detector for an imaging system includes a flexible substrate and a number of detector elements mounted to the substrate, each detector element configured to be independently operated.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
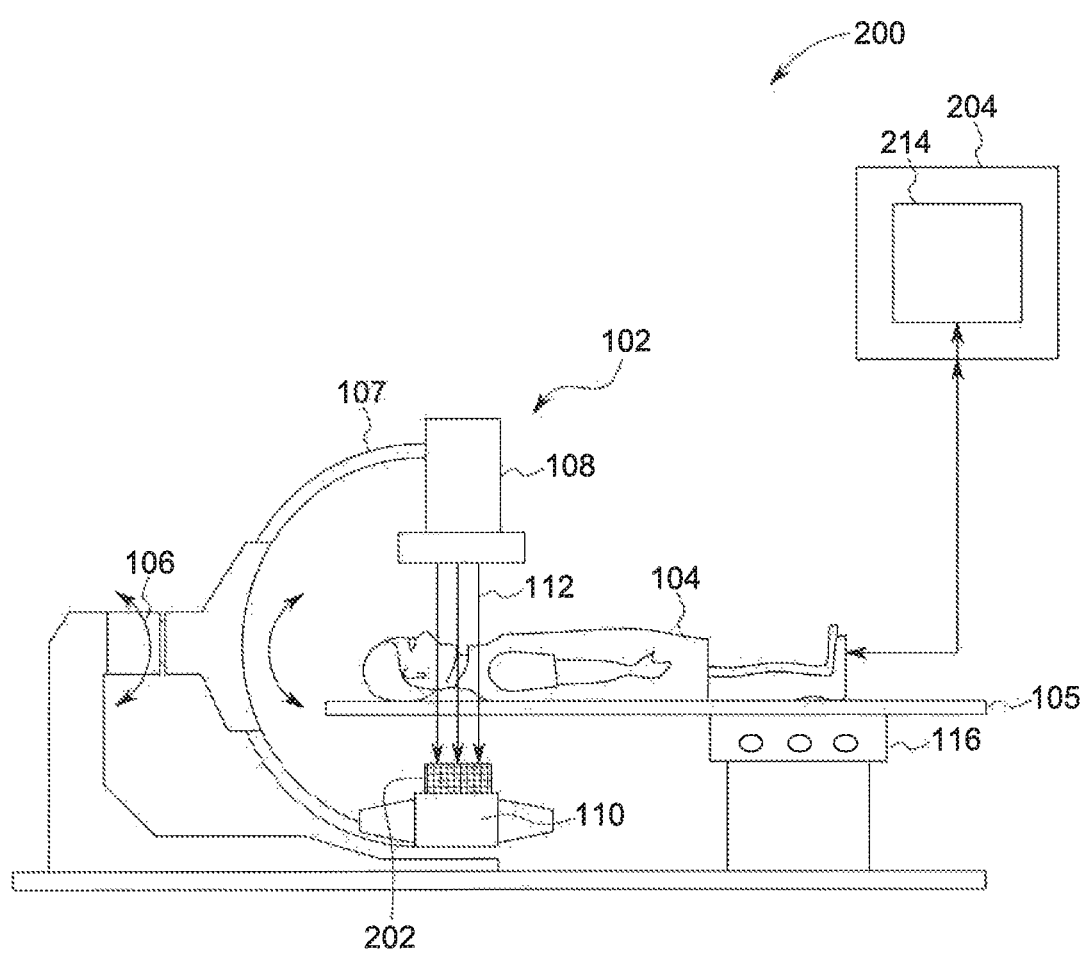
FIG. 1 is a schematic representation of a prior art imaging system.
Figure 2:
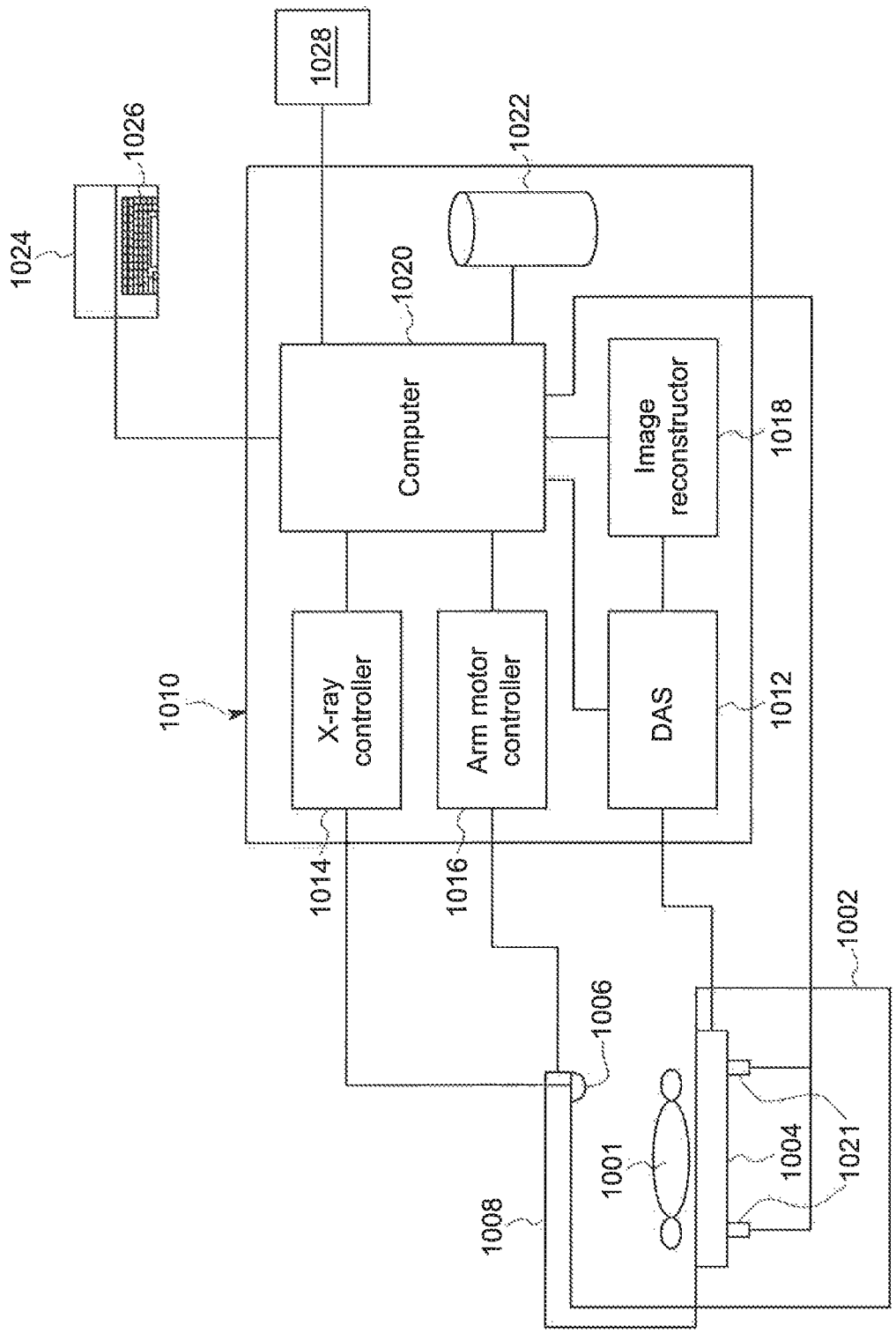
FIG. 2 is a schematic representation of an imaging system according to one embodiment of the invention.

Referring now to FIG. 2, an imaging system and/or scanner 1000 is illustrated in accordance with one exemplary embodiment of the invention. The imaging system 1000 includes a table 1002 for supporting a patient 1001 and in which is positioned an x-ray detector 1004(*s*) below the patient 1001. The x-ray detector 1004 is positioned across the entire area of the table 1002 such that the detector 1004 is positioned in alignment with, e.g., beneath, all parts of the patient 1001. The system 1000 also includes an x-ray source 1006 that is movably positionable relative to the table 1002 in order to direct x-rays 1012 from the source 1006 through the patient 1001 onto the detector 1004 at various positions relative to the table 1002. In the illustrated exemplary embodiment of FIG. 2, the source 1006 is disposed within an arm 1008 spaced above the table 1002 that is movable in the length and width directions and is angularly adjustable with respect to the table 1002. The table 1002, along with the detector 1004 and the x-ray source 1006 and arm 1008 are operably connected to a computer system 1010 that can control the operation of the x-ray source 1006 and/or arm 1008, and that can receive imaging data from the detector 1004 resulting from x-rays from the x-ray source 1006 passim through the patient 1001 and striking the detector 1004.

Figure 3:
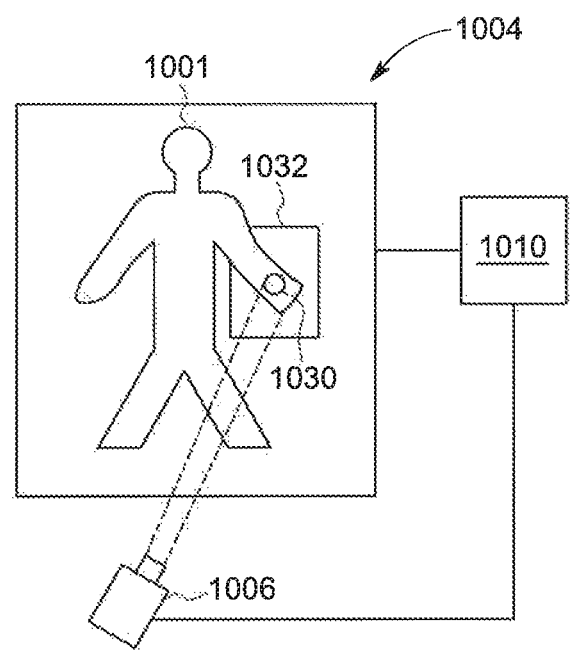
FIG. 3 is a schematic representation of the imaging system of FIG. 2.

Looking at FIGS. 2 and 3, in performing the scan to acquire x-ray projection data, the movement of the arm 1008 and the operation of the X-ray source 1006 are governed by the control mechanism/computer system 1010 of the imaging system 1000. The control mechanism 1010 includes an x-ray controller 1014 that provides power and timing signals to the x-ray source 1006 and an arm motor controller 1016 that controls the speed and position of the arm 1008. A data acquisition system (DAS) 1012 in the control mechanism 1010 samples analog data from the detector 1004 and converts the data to digital signals for subsequent processing. An image reconstructor 1018 receives sampled and digitized x-ray data from the DAS 1012 and performs high-speed reconstruction. The reconstructed image is applied as an input to a computer 1020, which stores the image in a database/mass storage device 1022.

Moreover, the computer 1020 also receives commands and scanning parameters from an operator via operator console 1024 that may have an input device such as a keyboard 1026. An associated display 1028 allows the operator to observe the reconstructed image and other data from the computer 1020. Commands and parameters supplied by the operator are used by the computer 1020 to provide control and signal information to the DAS 1016, the x-ray controller 1014 and the arm motor controller 1016.

Looking now specifically at FIG. 3, in one exemplary embodiment of the invention, the x-ray source 1006 is schematically shown with respect to the patient 1001 and the detector(s) 1004 during a scan of a region of interest (ROT) 1030 of the patient 1001. In performing the scan, the control mechanism 1010 determines the position of the source 1006 required to obtain the desired image of the ROI 1030. This function can also be performed manually by the operator using the control mechanism 1010 to position the source 1006 or by manually moving the source 1006 into the desired position. Once positioned, the control mechanism 1010 can locate an area 1032 of the detector 1004 that is in alignment with the source 1006 and the ROI 1030. The control mechanism 1010 can configure the area 1032 of the detector 1004 to be operable to receive/read x-rays 1011 emitted from the source 1006 and passing through the ROI 1030 to strike the area 1032. In one exemplary embodiment of the invention, the control mechanism 1010 can provide power to individual detector elements 1042 (FIG. 4) locate within the area 1032 defined by the position(s) of the source 1006 and the ROI 1030. In this manner, the detector 1004 can be configured to provide image data to the control mechanism 1010 for any portion of the patient 1001 being imaged with the area 1032 of the detector 1004 being selected based on the positions of the source 1006 and/or ROI 1030 determined by the control mechanism 1010.

Figure 4:
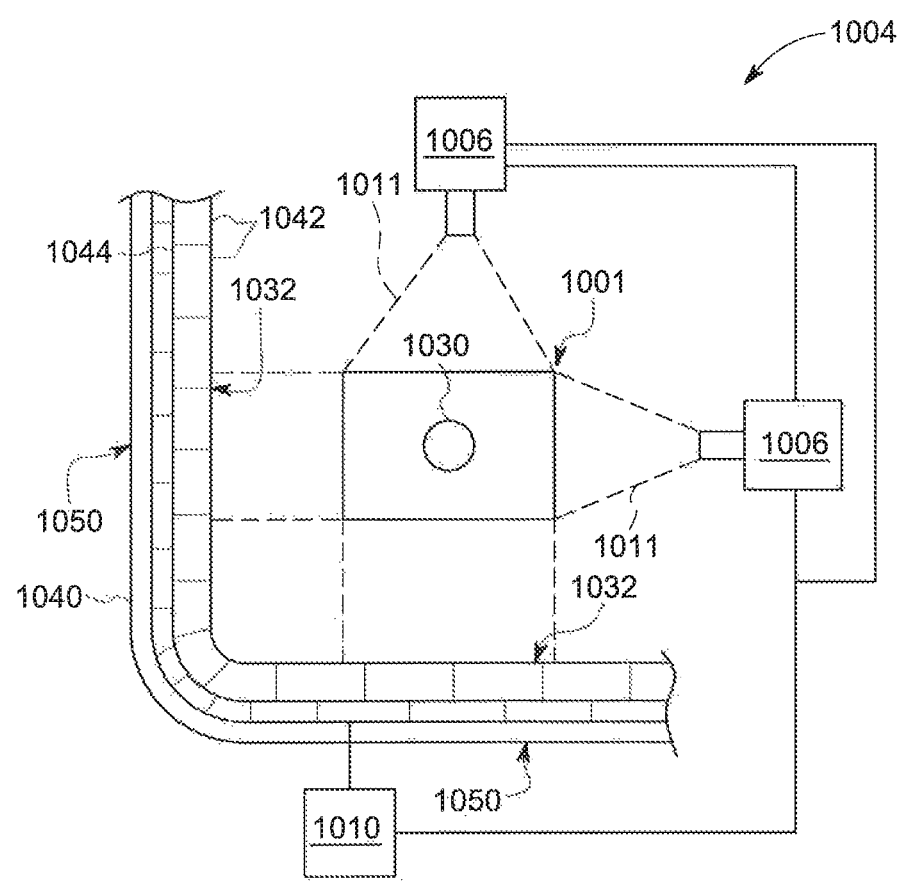
FIG. 4 is a schematic representation of a detector utilized with the imaging system according to another embodiment of the invention.

In an alternative exemplary embodiment, in FIG. 4, the detector 1004 is formed of a substrate 1040, such as a polymer substrate, and a number of detector elements 1042, such as organic or amorphous silicon photo diodes, disposed on the substrate 1040. The elements 1042 are individually connected to the control mechanism 1010, such as by a wired connection 1044, in order to supply image data from the elements 1042 to the control mechanism 1010. In addition, the connection 1044 can selectively apply power to individual elements 1042 from a suitable power source (not shown) under the direction of the control mechanism 1010, as described previously.

The substrate 1040 and the detector elements 1042 are formed to be flexible, such that the detector 1004 can be rolled, folded or bent in order to enable the detector 1004 to conform to various support surface shapes or be positioned in various configurations. In the illustrated exemplary embodiment of FIG. 4, the detector 1004 is folded into a generally right angle configuration. In this configuration for the detector 1004, an object/patient 1001 can be positioned between and/or adjacent each of the halves 1050 of the detector 1004. In this position, the source 1006 can be moved between different locations relative to the object/patient 1001 and the ROI 1030 in order to provide image data via the detector 1004 and particularly the area(s) 1032 of the detector 1004 aligned with the source 1006 in each imaging location without having to move either the object/patient 1001 or the detector 1004.

Figure 5:
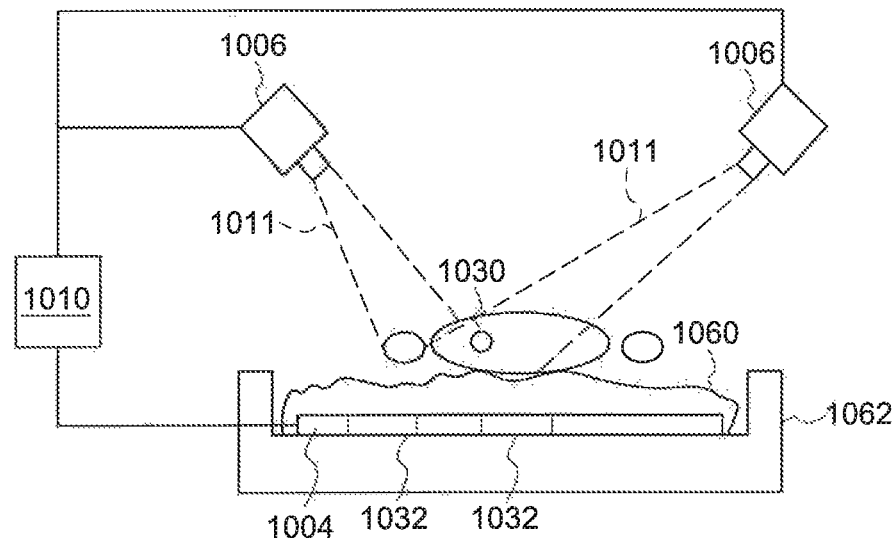
FIG. 5 is a schematic representation of an imaging system according to another embodiment of the invention.

Looking now at the exemplary embodiment illustrated in FIG. 5, the detector 1004 is disposed within a mattress 1060 for a patient bed 1062. The flexible nature of the detector 1004 prevents the detector 1004 from making the mattress 1060 rigid an unusable in the bed 1062, with the detector 1004 optionally being able to at least partially conform to the anatomy of the patient 1001. When employed within the mattress 1060, the detector 1004 enables images to be obtained of the patient 1001 without having to move the detector 1004 or move or remove the patient 1001 from the bed 1062, even when different positioned for the x-ray source 1006 are utilized. Further, the ability of the control mechanism 1010 to selectively operate the individual detector elements 1042 within the predetermined area(s) 1032 of the detector 1004 enables high quality image data/images to be obtained.

Figure 6:
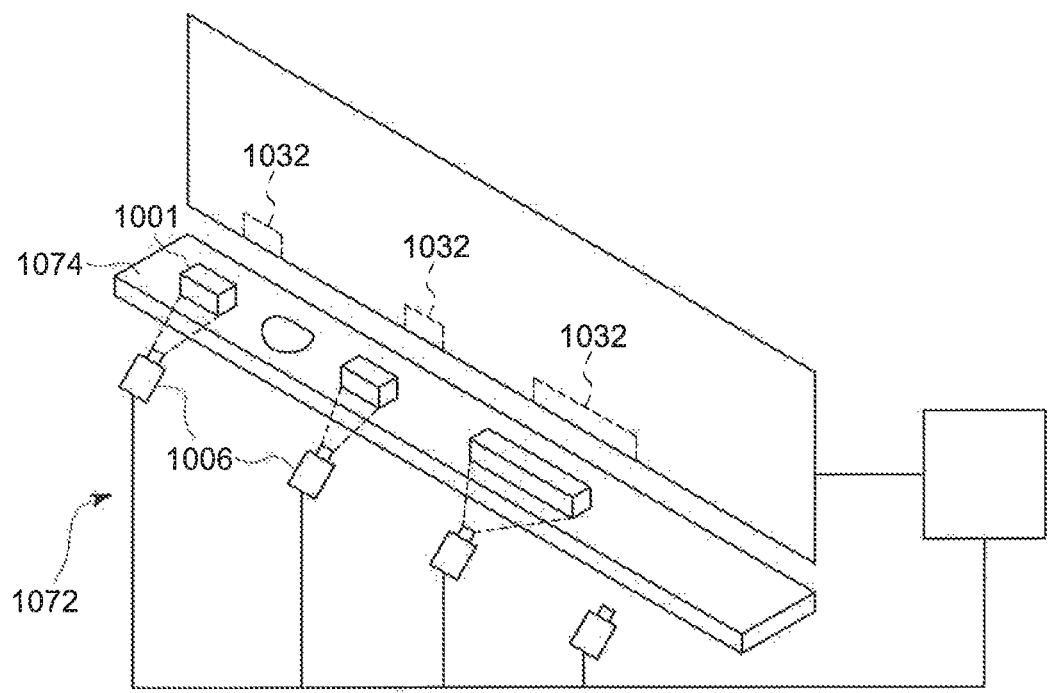
FIG. 6 is a schematic representation of an imaging system according to a further embodiment of the invention.

Referring now to the exemplary embodiment illustrated in FIG. 6, the detector 1004 is employed as a rear wall 1070 of a package scanning device 1072. In the device 1072, a conveyor belt 1074 moves a number of packages/objects 1001 between the detector 1004 and a number of x-ray sources 1006 disposed adjacent the conveyor belt 1074 opposite the detector 1004. As the packages/objects 1001 move along the conveyor belt 1074, the control mechanism 1010 can selectively operate area(s) 1032 of the detector 1004 in conjunction with the operation of the source(s) 1006 to obtain image data of the packages/objects 1001. In doing so, the control mechanism 1010 can operate the area(s) 1032 and the source(s) 1006 individually, consecutively and/or concurrently in order to more efficiently obtain image data of the packages/objects 1001 moving along the conveyor belt 1074 without moving the detector 1004. The modification of the mode of operation of the area(s) 1032 and/or the source(s) 1006 can be determined by the control mechanism 1010 based on any number of variables, including but not limited to the number of packages 1001 on the belt 1074, the size of the packages 1001 on the belts 1074, and the operational speed of the conveyor belt 1074, among others.

In another exemplary embodiment, the control mechanism 1010 can be operably connected to one or more sensing devices 1021, such as a pressure or thermal sensor, that are operably connected to the control mechanism 101 and/or computer 1020. The sensor(s) 1021 enable the control mechanism 1010/computer to automatically determine the position of the patient/object 1001 and/or the ROI 1030. The sensors 1021 enable the control mechanism 1010/computer 1020 to optionally control the position of the x-ray source 106 and/or the detector 1004 in order to align the source 1006 with the ROI 1030, as well as to determine the area of the detector 1004 aligned with the x-ray source 1006 and ROI 1030, optionally simultaneously, to select those detector elements 1042 in the area struck by the x-rays from the source 1006 passing through the ROI 1030 of the object/patient 1001, such as by automatically sensing the ROI 1030 and cropping and sending that ROI image data from the area of the detector 1004 formed by the selected detector elements 1042 to the control mechanism 1010/computer 1020 in order to form images of the ROI 1030. The presence of the sensors 1021 reduces system complexity with regard to the control of the position of the detector 1004, the source 1006 and/or the operation of the elements 1042 in the detector 1004.

In another exemplary embodiment, the control mechanism 1010/computer 1020 can selectively operate or obtain information from elements 1042 that are struck by x-rays from the source 1006, indicating the ROI 1030 as a result of the positioning of the source 1006 relative to the detector 1004.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for obtaining image data of a region of interest (ROI) within an object, the method comprising the steps of:
    providing an imaging system including an x-ray source, an x-ray detector including a number of independently operable detector elements and a control mechanism operably connected to the x-ray source and the detector elements for controlling operation of the x-ray source and receiving image data from the detector elements;
    positioning the x-ray source relative to the object to direct x-rays through the ROI;
    determining an area of detector elements in alignment with the x-ray source and the ROI;
    providing power to only the detector elements in the determined area; and
    operating the x-ray source to obtain x-ray image data of the ROI from the detector elements in the determined area.

2. The method of claim 1, wherein the detector remains stationary during the positioning of the x-ray source.

3. The method of claim 1, further comprising the step of positioning the object relative to the detector prior to positioning the x-ray source relative to the object.

4. The method of claim 3, wherein the step of positioning the object relative to the detector comprises placing the object over a portion of the detector.

5. The method of claim 4, wherein the object remains stationary after placing the object over a portion of the detector.

6. The method of claim 3, wherein the step of positioning the object relative to the detector comprises moving the object in front of a portion of the detector.

7. The method of claim 3 further comprising the step of sensing a position of the object after positioning the object relative to the detector.

8. The method of claim 7 wherein imaging system includes at least one sensing device, and wherein the step of sensing the position of the object comprises receiving a position signal from the at least one sensing device indicating the position of the object.

9. The method of claim 7 wherein the step of positioning the x-ray source relative to the object is performed after sensing the position of the object.

10. The method of claim 7 wherein the steps of positioning the x-ray source relative to the object and of determining the detector elements in alignment with the x-ray source occur simultaneously.

11. The method of claim 7 wherein the step of sensing a position of the object comprises determining those detector elements struck by x-rays from the source.

12. The method of claim 1, further comprising the steps of:
    moving the x-ray source relative to the detector after operating the x-ray source;
    re-determining an area of detector elements in alignment with the x-ray source and the ROI;
    operating the detector elements disposed within the re-determined area; and
    operating the x-ray source to obtain x-ray image data of the ROI from the detector elements in the re-determined area.

13. The method of claim 12 wherein the determined area is different from the re-determined area.

14. The method of claim 1 further comprising the steps of:
    providing an imaging system including multiple x-ray sources, an x-ray detector including a number of independently operable detector elements and a control mechanism operably connected to the x-ray sources and the detector elements for controlling operation of the x-ray sources and the detector elements and receiving image data from the detector elements;
    positioning the x-ray sources relative to multiple objects to direct x-rays through the ROI of the object;
    determining areas of detector elements in alignment with the x-ray sources and the ROIs;
    operating the detector elements disposed within the determined areas; and
    operating the x-ray sources to obtain x-ray image data of the ROIs from the detector elements in the determined areas.

15. An imaging system comprising:
    an x-ray source,
    an x-ray detector including a number of independently operable detector elements; and
    a control mechanism operably connected to the x-ray source and the detector elements for controlling operation of the x-ray source and the detector elements and receiving image data from the detector elements,
    wherein the control mechanism is configured to determine an area of detector elements in alignment with the x-ray source and an ROI of an object to be imaged and to provide power to only the detector elements disposed within the determined area.

16. The imaging system of claim 15 wherein the x-ray detector is flexible.

17. The imaging system of claim 16 wherein the detector includes a flexible substrate on which the detector elements are mounted.

18. The imaging system of claim 15 further comprising a power source operably connected to the detector elements via the control mechanism.

* * * * *